(12) United States Patent
Claycomb

(10) Patent No.: US 6,316,207 B1
(45) Date of Patent: *Nov. 13, 2001

(54) MOUSE CARDIAC MUSCLE CELL LINE, HL-1

(75) Inventor: William Creighton Claycomb, Carrier, MS (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 6 days.

(21) Appl. No.: 09/284,900
(22) PCT Filed: Oct. 24, 1997
(86) PCT No.: PCT/US97/19270
§ 371 Date: Apr. 22, 1999
§ 102(e) Date: Apr. 22, 1999
(87) PCT Pub. No.: WO98/18906
PCT Pub. Date: May 7, 1998

Related U.S. Application Data
(60) Provisional application No. 60/029,058, filed on Oct. 25, 1996.

(51) Int. Cl.$^7$ .................. G01N 33/53; G01N 33/567; C12N 5/06
(52) U.S. Cl. ............ 435/7.2; 435/374; 435/375; 435/383; 435/362; 435/7.1
(58) Field of Search .................. 435/325, 352, 435/354, 374, 384, 385, 386, 387, 375, 383, 362, 7.1, 7.2; 800/3, 4, 13, 18

(56) References Cited

FOREIGN PATENT DOCUMENTS
WO 92/22636  12/1992 (WO).
WO 98/18906  5/1998 (WO).

OTHER PUBLICATIONS

Daud et al. Am J Physiol 264 (65, pt. 2) H1693–H1700, 1993.*

Katz et al. Am J Physiol 262 (6, Pt. 2) H 1867–H 1876, 1992.*

Lanson et al. Cirulation 85 (5):1835–41, 1992.*

Cook et al. Am J Physiol 268 (4, Pt. 2) H1471–H1482, 1995.*

Folkman, J., Shing, Y., "Minireview: Angiogenesis", *The Journal of Biological Chemistry*, vol. 267, No. 16., pp. 10931–10934, (Jun. 5, 1992).

Claycomb, W.C., Bradshaw, H.D., Jr., "Aquisition of Multiple Nuclei and the Activity of DNA Polymerase α and Reinitiation of DNA Replication in Terminally Differentiated Adult Cardiac Muscle Cells in Culture", *Developmental Biology* 99, pp. 331–337, (1983).

Claycomb, W.C., "Control of Cardiac Muscle Cell Division", *TCM*, vol. 2, No. 6, pp. 231–236, (1992).

Claycomb, W.C., Moses, R.L., "Growth Factors and TPA Stimulate DNA Synthesis and Alter Morphology of Cultured Terminally Differentiated Adult Rat Cardiac Muscle Cells", *Developmental Biology* 127, pp. 257–265. (1988).

Chadwick, C.C., et al., "Identification of a Specific Radioligand for the Cardiac Rapidly Activating Delayed Rectifier $K^{30}$ Channel", *Circulation Research*, vol. 72, No. 3, (Mar., 1993).

Koh, G.Y., Soonpaa, M.H., Klug, M.G., Filed, L.J., "Long-–term Survival of AT–1 Cardiomyocyte Grafts in Syngeneic Myocardium", *Am. J. Physiolog.* 264, pp. H1727–H1733. (1993).

Delcarpio, J.B., Lanson, N.A., Jr., Field, L.J., Claycomb, W.C., Morphological Characterization of Cardiomyocytes Isolated From a Transplantable Cardiac Tumor Derived from Transgenic Mouse Aria (AT–1 Cells).*Circulation Research*, vol. 69, No. 5, (Dec., 1991).

Cross, P.E., et al., "Selective Class III Antiarrhythmic Agents", *J. Med. Chem.*, vol. 33, No. 4, pp. 1151–1155, (1990).

Fermini, B., et al., "Use–Dependent Effects of the Class III Antiarrhythmic Agent NE–10064 (Azilimide) on Cardiac Repolarization: Block of Delayed Rectifier Potassium and L–Type Calcium Currents", *Journal of Cardiovascular Pharmacology*, vol. 26, pp. 259–271, (1995).

* cited by examiner

*Primary Examiner*—Patricia A. Duffy
(74) *Attorney, Agent, or Firm*—Cynthia M. Bott; Carl J. Roof; Karen F. Clark

(57) ABSTRACT

This invention involves a mouse cardiac cell line (HL-1) derived from a transplantable mouse cardiomyocyte lineage (AT-1) which can be serially passaged in culture greater than two hundres times and retain the characteristics of adult atrial cardiac muscle cells. This invention also relates to a cell culture system which can be used as an in vitro model of cardiac muscle cells to screen and test cardiac drugs. This invention also relates to the use of this mouse cardiac cell line to produce factors in cardiac cells.

5 Claims, 8 Drawing Sheets

SEQUENCE LISTING

```
<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence:  PCR
      primers for alpha cardiac myosin heavy chain

<400> SEQUENCE: 1
ctgctggaga ggttattcct cg                                           22

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:  PCR
      primers for alpha cardiac myosin heavy chain

<400> SEQUENCE: 2
ggaagagtga gcggagcatc aagg                                         24

<210> SEQ ID NO 3
<211> LENGTH: 24
```

```
<212> TYPE: DNA
<213> ORGANISM: Artificial Sequence
<220> FEATURE:
<223> OTHER INFORMATION: Description of Artificial Sequence:  PCR
      primers for beta cardiac myosin heavy chain

<400> SEQUENCE: 3
tcgaaaggct ccaggtctga gggc                                          24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:  PCR
      primers for beta cardiac myosin heavy chain

<400> SEQUENCE: 4
gccaacacca acctgtccaa gttc                                          24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:  PCR
      primers for alpha cardiac actin

<400> SEQUENCE: 5
tgttacgtcg ccttggattt tgag                                          24

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence:  PCR
      primers alpha cardiac actin

<400> SEQUENCE: 6
aagagagaga catatcagaa gc                                            22

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:  PCR
      primers for skeletal alpha actin

<400> SEQUENCE: 7
tattccttcg tgaccacagc tgaacgt                                       27

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:  PCR
      primers for skeletal alpha actin

<400> SEQUENCE: 8
cgcgaacgca gacgcgagtg cgc                                           23

<210> SEQ ID NO 9
<211> LENGTH: 30
<212> TYPE: DNA
```

```
<213> ORGANISM: Artificial Sequence
<220> FEATURE:
<223> OTHER INFORMATION: Description of Artificial Sequence:  PCR
      primers for atrial natriuretic factor

<400> SEQUENCE: 9
cgtgccccga cccacgccag catgggctcc                                    30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:  PCR
      primers for atrial natriuretic factor

<400> SEQUENCE: 10
ggctccgagg gccagcgagc agagccctca                                    30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:  PCR
      primers for connexin43

<400> SEQUENCE: 11
gttcaagtac gggattgaag agcacggcaa                                    30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence:  PCR
      primers for connexin43

<400> SEQUENCE: 12
tggttttctc cgtgggacgt gagaggaagc                                    30
```

MOUSE CARDIAC MUSCLE CELL LINE, HL-1

This application claims priority, under Title 35, United States Code119(e) from provisional application Ser. No. 60/029,058, filed Oct. 25, 1996.

TECHNICAL FIELD

The present invention relates to a novel cell line ("HL-1") derived from a transplantable mouse cardiomyocyte lineage (AT-1) wherein the cell line has the following characteristics: a) can be serially passaged greater than two hundred times and retain the ability to spontaneously contract: b) can be frozen, stored in, and recovered from liquid nitrogen, and revived upon thawing; c) can be cultured in serum-free medium; d) retains ultrastructural characteristics of in vitro adult atrial cardiac muscle cells; e) displays a pattern of gene expression similar to that of adult atrial myocytes including ANF, atrial natriuretic factor, α-cardiac myosin heavy chain, α-cardiac actin and connexin43; f) responds positively to immunohistochemical stains for desmin, sarcomeric myosin, and atrial natriuretic peptide; g) will give rise to tumors when injected subcutaneously into syngeneic mice; h) can secrete into the culture medium growth factors including basic fibroblast growth factor (bFGF), vascular endothelial growth factor (VEGF), platelet derived growth factor (PGDF), epithelial growth factor (EGF), transforming growth factor beta 1(TGF-β1), and adrenomedullin; i) displays a cardiac-like, rapidly activating and inactivating delayed rectifier potassium current with biophysical and pharmacological characteristics that are nearly identical to those described for cardiac $I_{Kr}$; j) displays time- and voltage-dependent inward currents that are most likely sodium and L-type calcium currents.

The present invention further relates to a cell culture system which can be used as an in vitro model of the cardiac muscle cell to screen and test cardiac drugs. This invention relates generally to a novel cell line, and specifically to a novel mouse cardiac muscle line, as well as to the use of these cells to produce and isolate factors in cardiac cells and/or screen cardiac drugs.

BACKGROUND OF THE INVENTION

Attempts to create a cardiac muscle cell line which actively proliferates in culture while maintaining the differentiated phenotype have to date not been successful. Transgenic mouse lines have been derived in which the simian virus SV40 large T antigen expression has been targeted to atrial and ventricular cardiomyocytes of the heart [Field, Science 239:10029–10033 (1988); Katz, et al. Am J. Physiol 262:H1867–H1876 (1992)]. Expression of this oncogene under control of the atrial natriuretic factor (ANF) promoter results in atrial hyperplasia whereas expression of this oncogene under control of the α-cardiac myosin heavy chain promoter results in hyperplastic growth of both atrial and ventricles. AT-1 cells are atrial cardiomyocytes that were derived from the ANF-SV40 large T antigen construct [Delcarpio, et al. Circ. Res. 69:1591–1600 (1991)]. These highly differential myocytes have been maintained for over 6 years by serial passage as ectopic grafts in syngeneic mice. AT-1 cells can be easily cultured and maintain their cardiac phenotype; however, they can not be passaged in culture and must be maintained as a subcutaneous tumor lineage in syngeneic mice. On the other hand, a cardiac muscle cells line named AT-2 cells has been derived from atrial tissue of transgenic mice expressing SV40 large T antigen under control of the α-cardiac myosin heavy chain promoter. At-2 cells rapidly divide in culture (average population doubling time of 24 hours) and can be easily passaged, but they totally lose their phenotype after about the tenth passage in culture [Katz, et al. Am J. Physiol. 262:H1867–H1876 (1992); Borisov and Claycomb, Annals of N.Y. Acad. Sci., 752:80–91 (1995)]. Attempts by others to produce a cardiac myocyte cell line have resulted in a similiar pattern of loss of phenotype. One of the first reports of a cardiac myocyte cell line was on the isolation of a clonal cell line from rat heart [Kimes and Brandt, Exp. Cell Res 98:367–381 (1976)]. These cells fused to form typical skeletal myotubes and they expressed skeletal muscle-specific creatine phosphokinase. Contamination of these cardiomyocyte cell line cultures with skeletal myoblasts was not, however, rigorously excluded. v-myc transformed quail cardiac myoblasts have been passaged over 60 times [Jaffredo, et al. Exp. Cell Res. 192:481–491 (1991)]. This line originates from myocardial tumors induced in 3 day-old quail embryos by microinjection of MC29 avian retrovirus carrying the myc-oncogene. These cells progressively lose their muscle markers with time in culture although co-culture of these cells with 3T3 mouse fibroblasts induces a moderate re-expression of muscle myosin. However, the localization of this protein is diffuse, and the cells did not form an organized contractile cytoskeleton and never exhibited contractile activity. Similar results on the establishment of a cell line from precardiac splanchnic mesoderm of a Japanese quail embryo was recently reported [Eisenberg, Anat. Rec. 232:30A (1992)]. During the establishment of this cell line muscle-specific markers were also lost. They could be induced to express desmin, sarcomeric myosin heavy chain and muscle actin by altering the culture conditions. Neither myofibrils nor contractile activity was detected in these cultured cells. Recently it was reported that human fetal cardiac muscle cells transfected with SV 40 T antigen could be maintained for over a year in culture. [Wang, et al. In Vitro Cell. Dev. Biol. 27:63–74 (1991) ]. These cells expressed several markets of early fetal human cardiac myocytes but did not retain contractile activity. Embryonic rat cardiac myocytes transfected with the v-myc and v-H-ras oncogenes have been reported to undergo multiple passages in culture and to retain the expression of several cardiac-specific genes [Engelmann, et. al. J. Mol. Cell. Cardiol. 25:197–213 (1993)]. In summary, to date no cardiac muscle cell line has been reported or is available that: 1) retains a highly differentiated adult cardiac myocyte phenotype; 2) maintains contractile activity; and 3) can be serially passaged in culture.

OBJECTS OF THE PRESENT INVENTION

It is the object of the present invention to provide a novel cardiac muscle cell line. It is a further object of the present invention to produce a novel cell culture system which can be used as an in vitro model of cardiac muscle to screen and to test cardiac drugs. It is a further object of this invention to use this novel mouse cardiac muscle line to produce and, to isolate factors in and from cardiac cells, and/or to screen cardiac drugs.

BRIEF DESCRIPTION OF THE FIGURES

FIG. 5 Ion currents were activated by 1 sec voltage pulses from a holding potential of –50 mV to potentials between –40 mV to +40 mV in 20 mV increments. In the figure, time-dependent outward currents were activated during the test voltage pulse (0–1000 msec) are seen as upward deflections, while deactivating "tail" currents appear (1000–2000 msec) as the test voltage is returned to the holding voltage. A holding potential of –50 mV was used to inactivate $Na^+$ and T-type $Ca^{++}$ currents. 100 $\mu$M $Cd^{++}$ was included in the extracellular solution to block L-type $Ca^{++}$ current. The activating current displayed inward rectification and deactivating current "tails" were voltage dependent and saturated at +20 mV. The deactivation kinetics of the "tail" current were biexponential. FIG. 6 In the presence of methanesulfonanilide, cardiac $I_{Kr}$ is identified, based on the high selectivity of the mathanesulfonanilide group of Class III antiarrhythmic compounds for this channel. [Jurkiewicz, N. K. and Sanguinetti, M. C., Circ. Res. 72 (75–83) (1993)]. The methanesulfonanilide, dofetilide (10 $\mu$M) completely abolished the time-dependent component of the activating current as well as the deactivating tail currents. Upon complete blockade of time-dependent outward current by dofetilide, a residual time-independent outward current was noted. The ionic nature of the current carrier was not identified.

SUMMARY OF THE INVENTION

Figure 1:
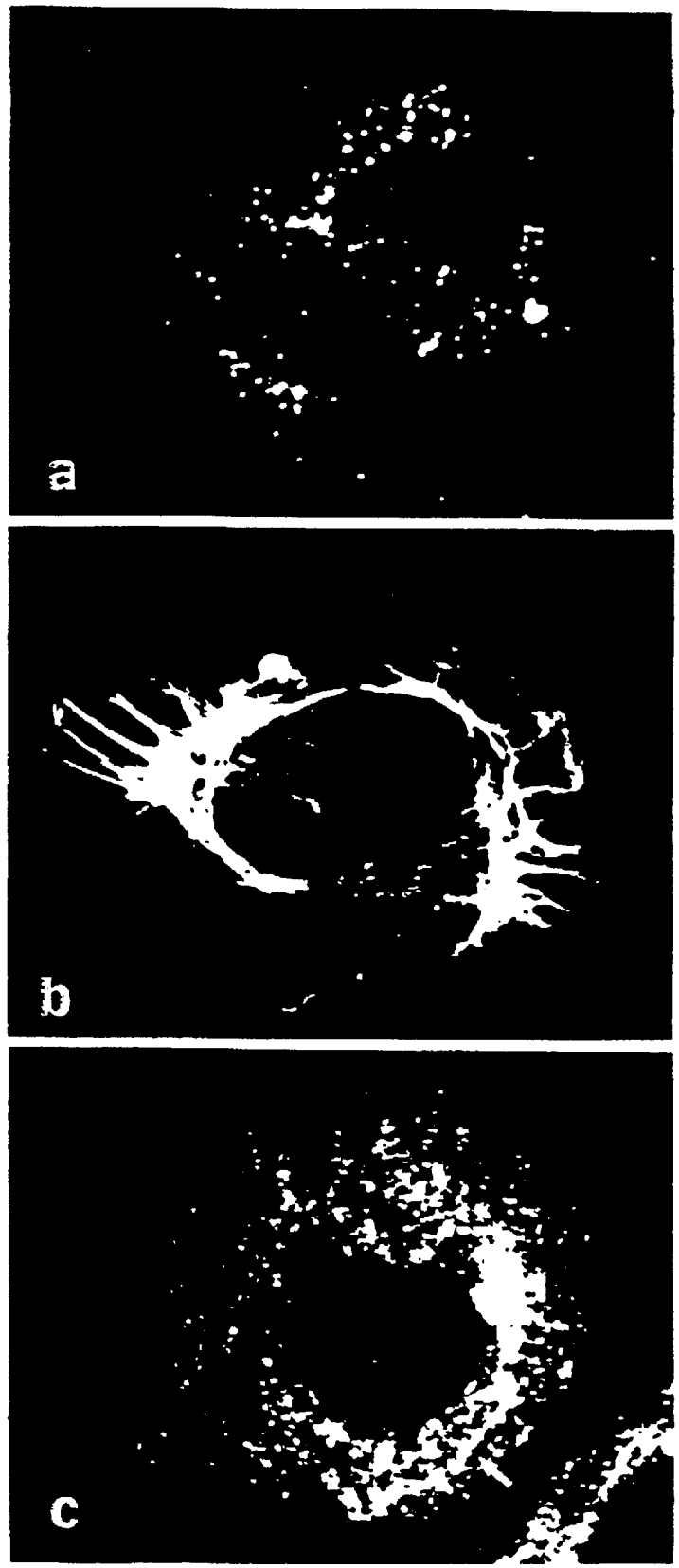
FIGS. 1 a.–c. Expression of cardiac specific proteins in cultured HL-1 cardiomyocytes after passage 20. a. HL-1 cells express atrial-specific atrial natriuretic peptide-containing granules. b. Desmin is expressed as cytoplasmic rings of intermediate filaments which extend into the filopodia of the cardiomyocyte. c. Myosin is localized to scattered filaments in the cytoplasm and to thin myofibrils located along the peripheral cytoplasm (arrowhead). All are indirect immunofluorescence confocal laser scanning microscopy images.

The present invention relates to a novel cell line ("HL-1") derived from a transplantable mouse cardiomyocyte lineage (AT-1) wherein the cell line has the following characteristics: a) can be serially passaged greater than two hundred times and retain the ability to spontaneously contract; b) can be frozen, stored in, and recovered from liquid nitrogen, and revived upon thawing; c) can be cultured in serum-free medium; d) retains ultrastructural characteristics of in vitro adult atrial cardiac muscle cells; e) displays a pattern of gene expression similar to that of adult atrial myocytes including atrial natriuretic factor, α-cardiac myosin heavy chain, α-cardiac actin and connexin43; f) responds positively to immunohistochemical stains for desmin, sarcomeric myosin, and atrial natriuretic peptide; g) will give rise to tumors when injected subcutaneously into syngeneic mice; h) can secrete into the culture medium growth factors including basic fibroblast growth factor (bFGF), vascular endothelial growth factor (VEGF), platelet derived growth factor (PDGF), epithelial growth factor (EGF), transforming growth factor beta 1(TGF-β1). and adrenomedullin; i) displays a cardiac-like, rapidly activating and inactivating delayed rectifier potassium current with biophysical and pharmacological characteristics that are nearly identical to those described for cardiac $I_{Kr}$; j) displays time- and voltage-dependent inward currents that are most likely sodium and L-type calcium currents.

The present invention further relates to a cell culture system which can be used as an in vitro model of cardiac muscle cells to screen and test cardiac drugs. The present invention also relates to the use of this novel mouse cardiac cell line to produce and/or to isolate factors in cardiac cells.

DETAILED DESCRIPTION OF THE INVENTION

As used herein, "HL-1" refers to the novel cell line of the present invention. It has been named "HL-1 F2 P76."

The present invention relates to a novel cell line isolated from a transplantable tumor lineage wherein the cell line has the following characteristics:

a) can be serially passaged greater than two hundred times, while retaining the ability to spontaneously contract and maintain the cardiomyocyte phenotype;

b) can be frozen and stored in liquid nitrogen, and can be revived upon thawing;

c) retains ultrastructural characteristics of adult mouse cardiac atrial muscle cells;

d) displays a pattern of gene expression similar to that of adult cardiac atrial myocytes including expression of atrial natriuretic factor (ANF), or α-cardiac myosin heavy chain, α-cardiac actin and connexin43;

e) responds positively to immunohistochemical stains for desmin, sarcomeric myosin, and atrial natriuretic peptide;

f) at passages up to 87, will give rise to tumors when injected subcutaneously into syngeneic mice which can subsequently be cultured to give contracting HL-1 cells;

g) secretes into the culture medium growth factors including basic fibroblast growth factor (bFGF), vascular endothelial growth factor (VEGF), platelet derived growth factor (PDGF), epithelial growth factor (EGF), transforming growth factor beta 1(TGF-β1), and adrenomedullin;

h) displays a cardiac-like, rapidly activating and inactivating delayed rectifier potassium current with biophysical and pharmacological characteristics that are nearly identical to those described for cardiac $I_{Kr}$;

i) displays time- and voltage-dependent inward currents that are most likely sodium and L-type calcium currents.

ESTABLISHMENT OF THE HL-1 CELL LINE

A cell line, HL-1, was established from an AT-1 subcutaneous tumor excised from an adult female Jackson Lab inbred C57BL/6J mouse. The tumor tissue was removed from the euthanized animal and carefully trimmed of connective tissues. The excised tissue was minced and incubated at 4° C. for 14 hours in 0.125% trypsin in Joklik's media with gentle agitation. Cells were obtained by sequential digestion with 0.1% collagenase in Joklik's media at 37° C., pooled and plated at $2.0 \times 10^6$ cells/5 ml in gelatin/fibronectin-coated T25 flasks, 2 ug each/cm$^2$ flask (fibronectin from Sigma, catalog # F-1141; gelatin from Difco, catalog # 0143-01). The HL-1 cell line was established after more than one hundred attempts to serially passage tumor-derived cells in culture. The culture conditions were altered to maintain cellular proliferation and contractile activity in the cell cultures (optimum culture conditions are described below). Betwen passages 20 to 30, the cells became noticeably vacuolated, grew slowly and were morphologically heterogeneous; after Passage 40, the morphology of the HL-1 cells became more uniform.

The cells are optimally maintained, with respect to proliferation and differentiated phenotype, in ExCell 320 medium (JRH Biosciences, cat 190 14-320) supplemented with 10% fetal bovine serum (FBS) (Whittaker lot 190 181m11), 10 –100 ug/ml Insulin (GIBCO # 680-330-7AC), 100–1000 ug/ml Endothelial Cell Growth Supplement (Upstate Biotechnology, #02-101), 10–100 uM retinoic acid (Sigma # R2625). norepinephrine 1–100 uM, 100 U/ml penicillin, 100 ug/ml streptomycin (GIBCO # 1531), and 1 xnon-essential amino acids (GIBCO # 320–1140 AG). The medium is changed approximately every 48 hours. The cells are grown at 37° C. in an atmosphere of 5% $CO_2$ and 95% air at a relative humidity of approximately 95%. Once the HL-1 cells reached confluence in the tissue culture were split. A culture split of 1 to 3 is designated as a passage.

Soybean trypsin inhibitor (GIBCO # 840-7075IH), 0.0025 g/100 ml PBS is used to inactivate trypsin. Cells are centrifuged gently in serum-containing growth medium to further inhibit trypsin. HL-1 cells have been passaged over 200 times with no known limited life span. Confluent, beating cultures are subcultured (split) 1:3 using 0.05% trypsin for 5 to 6 minutes at 37° C. The HL-1 cell line was tested for mycoplasma contamination at passage 13, 51 and 96 by Bionique Testing Laboratories, inc. (Saranac Lake, N.Y.) and found to be negative.

The HL-1 cell line was found to be tumorigenic when assayed for tumor formation in syngeneic mice. HL-1 cells at various passages up to passage 87 were injected subcutaneously in the neck region of the animals at an inoculum of approximately $1 \times 10^6$ cells per site. Tumors arose at the site of injection within two months. Over 50% of animals injected with the HL-1 cells were observed to develop tumors within two months after a subcutaneous injection.

MORPHOLOGICAL CHARACTERISTICS OF THE HL-1 CELL LINE

Figure 2:
FIGS. 2 a.–f. Expression of a cardiac-specific phenotype at multiple passages in the HL-1 cardiomyocyte cell line. A. HL-1 cells contain thin, peripherally located myofibrils (arrowhead), numerous free ribosomes (small arrowheads), and euchromatic nuclei (N), typically associated with dividing cells; Passage 10. b. Because these cells are capable of proliferation, their cytoplasms are filled with myofibrils at various stages of sarcomerogenesis (arrowheads) but remain attached to adjacent cardiomyocytes via immature intercalated discs (double arrowheads); Passage 10. c. HL-1 cells continue to express atrial natriuretic factor (ANF) (arrowheads). d. Dividing HL-1 cells behave like typical cardiomyocytes in that they retain peripheral myofibrils (arrow), are anchored to adjacent cardiomyocytes by intercalated discs (arrowheads). Small arrowheads, atrial granules; ("c" indicator) chronmosomes; Passage 34. e. At later passages, active Golgi and atrial-specific granules are still present (arrowheads). Passage 86. f. These later passage HL-1 cells continued to display thinly organized myofibrils (arrowheads) which are confined to the peripherl regions of the cell and at the intercalated disc (arrow). Large areas occupied by free ribosomes (*) are also present. Passage 86.

The HL-1 cell line displays a differential morphological phenotype (See FIGS. 1 and 2 for details). The HL-1 cells in the presence of norepinephrine retain the ability to contract through at least passage 200. Ultrastructural characteristics typical of atrial cardiac muscle cells were observed in the cultured HL-1 cells although they were not as prevalent as in an in situ atrial myocyte. These include perinuclear atrial granules, loosely organized sarcomeric structures which contain actin and myosin filaments, nascent gap junctions, and intercalated discs, and subsarcolemmal sarcoplasmic reticulum diffusely distributed throughout the cytoplasm. Immunohistochemically the HL-1 cells are positive for sarcomeric myosin, the muscle-specific intermediate filament protein desmin and atrial natriuretic peptide.

FLUORESCENCE MICROSCOPY

For indirect immunofluorescence the HL-1 cells grown on coverslips were fixed with 2.5% paraformaldehyde in phosphate buffered saline (pH 7.2) for 15 min at 4° C. and permeabilized with 0.1% Triton X-100 for 3 minutes. The primary antibodies used for indirect immunofluorescent staining were: monoclonal anti-desmin from Sigma (catalog number D1033, lot 103H-4845) used at a 1:40 dilution, monoclonal antibody MF 20 to sarcomeric myosin heavy chain used at a dilution of 1:20 (kindly provided by Drs. D. A. Fischman and D. M. Bader of Cornell University Medical College, New York) and monoclonal antibody to atrial natriuretic peptide used at a 1:200 dilution (kindly provided by Dr. C. C. Glembotski, University of California, San Diego). The secondary antibody was FITC-conjugated goat anti-mouse IgG used at a 1:64 dilution (Sigma, catalogue number T6528, lot 051H-8935).

Results of these analyses indicate that the HL-1 cells express cardiac myocyte specific proteins that are organized and spatially arranged in a manner typical for adult cardiomyocytes in culture. (See FIG. 1). The HL-1 cells are observed to express atrial specific atrial natriuretic peptide containing granules. The muscle specific protein desmin is expressed as cytoplasmic rings of intermediate filaments which extend into the filopodia of the cardiomycyte. The muscle specific protein myosin is localized to scattered filaments in the cytoplasm and to thin myofibrils located along the peripheral cytoplasm demonstrating that the HL-1 cells are capable of organizing sarcomeric structures.

TRANSMISSION ELECTRON MICROSCOPY

Selected cultures were prepared for in situ electron microscopy as described previously (Am. J. Anat. 186:

335–345, 1989). Briefly, cells were fixed in 4.0% glutaraldehyde/0.1 M sodium cacodylate, postfixed in 1.0% osmium tetroxide/0.1 M sodium cacodylate, stained en bloc using 0.5% aqueous uranyl acetate. Following dehydration in a graded alcohol series, the sections were infiltrated and embedded in Polybed 812 plastics (Polysciences Inc., Warrington, Pa.). Thin sections were cut using a Reichert Ultracut ultramicrotome equipped with a diamond knife, collected on uncoated 200 mesh copper grids, post stained with lead citrate, and examined in a Philips 301 transmission electron microscope at 80 kV.

Results of this ultrastructural study at various passages further demonstrate that HL-1 cells exhibit a cardiac specific phenotype (See FIG. 2 for details). The HL-1 cells contain thin peripherally located myofibrils, numerous free ribosomes, and euchromatic nuclei, all of which are indicative of a phenotype, typically associated with dividing cells. Because these HL-1 cells are capable of proliferation, the cytoplasm is filled with myofibrils at various stages of sarcomerogenesis. The cells remain attached to adjacent cardiomyocytes via immature intercalated discs.

DETECTION OF CONTRACTILE PROTEIN ISOFORMS AND ANF AND CONNEXIN43 GENE EXPRESSION

Contractile protein isoform expression is a well established characteristic of the developmental and differentiated state of cardiomyocytes. In order to characterize the HL-1 cell line in terms of the cardiac-specific genes they express, a reverse transcriptase-polymerase chain reaction (RT-PCR)-based analysis was used. For each assay, total RNA was isolated as decribed by Lanson, et al. [Cir. 85:1835–1841(1992)]. For each reaction, 50 ng of total RNA was resuspended in 100 ml of 50 mM KCl, 10 mM Tris-HCl (pH 8.3), 2.5 mM $MgCl_2$, and 0.01 mg/ml gelatin. Antisense oligonucleotide primer (0.3 ng), sense oligonucleotide primer (0.2 ng), and 2.5 units of Taq DNA polymerase (Amplitaq®, Perkin-Elmer Corp., Norwalk, Conn.) were then added to each reaction mixture. The solution was brought to 85° C. for 5 minutes and then equilibrated at room temperature for 10 minutes. Ten units of reverse transcriptase (International Biotechnologies, Inc., New Haven, Conn.) were added, and samples were overlaid with paraffin oil and incubated in a Perkin-Elmer DNA thermocycler. For this reaction, the initial incubation was for 60 minutes at 42° C. followed by 10 minutes at 94° C. The thermocycler was programmed to amplify the synthesized cDNA; the temperature and cycle lengths were optimized for each pair of oligonucleotide primers as described below.

To generate PCR amplification products from α-cardiac myosin heavy chain (α-MHC), the sense oligonucleotide was 5'-CTGCTGGAGAGGTTATTCCTCG-3', (SEQ ID NO:1) the antisense oligonucleotide was 5'-GGAAGAGTGAGCGGCGCATCAAGG-3' (SEQ ID NO:2), and the amplification program consisted of 30 cycles of 94° C. for 1 minute, 62° C. for 1 minute and 72° C. for 1 minute. The PCR product was expected to be 302 base pairs. To generate PCR amplification products from β-cardiac myosin heavy chain (β-MHC), the sense oligonucleotide was 5'-TGCAAAGGCTCCAGGTCTGAGGGC-3', (SEQ ID NO:3) the antisense oligonucleotide was 5'-GCCAACACCAACCTGTCCAAGTTC-3'( SEQ ID NO:4), and the amplification program was the same as for α-MHC. This PCR product was expected to be 205 base pairs. Sequences from which these primers were derived were described by Robbins, et al. [J. Biol. Chem. 265:11905–11909 (1990)].

To generate PCR amplification products from α-cardiac actin, the sense oligonucleotide was 5'-TGTTACGTCGCCTTGGATTTTGAG-3' (SEQ ID NO:5), the antisense oligonucleotide was 5'-AAGAGAGAGACATATCAGAAGC-3' (SEQ ID NO:6), and the amplification program consisted of 30 cycles of 94° C. for 1 minute, 50° C. for 2 minutes, and 72° C. for 3 minutes. The PCR product was expected to be 494 base pairs. To generate PCR amplification products from skeletal α-actin, the sense oligonucleotide was 5'-TATTCCTTCGTGACCACAGCTGAACGT-3' (SEQ ID NO:7), the antisense oligonucleotide was 5'-CGCGAACGCAGACGCGAGTGCGC-3' (SEQ ID NO:8), and the amplification program was the same as for α-cardiac actin. This PCR product was expected to be 562 base pairs. Sequences from which these primers were derived were described by Alonso, et al. [J. Mol. Evol. 23:11–22 (1986)].

To generate PCR amplification products from ANF, the sense oligonucleotide was 5'-CGTGCCCCGACCCACGCCAGCATGGGCTCC-3', (SEQ ID NO:9) the antisense oligonucleotide was 5'-GGCTCCGAGGGCCAGCGAGCAGAGCCCTCA-3', (SEQ ID NO:10), and the amplification program was the same as for α- and β-MHC. The PCR product was expected to be 389 base pairs. Sequences from which these primers were derived were described by Seidman, et al. [Science 226:1206–1209 (1984)].

To generate PCR amplification products from connexin43, the sense oligonucleotide was 5'-GTTCAAGTACGGGATTGAAGAGCACGGCAA-3' (SEQ ID NO:11), the antisense oligonucleotide was 5'-TGGTTTTCTCCGTGGGACGTGAGAGGAAGC-3' (SEQ ID NO:12), and the amplification program consisted of 30 cycles of 94° C. for 1 minute, 62° C., for 1 minute, and 72° C. for 1 minutes. The PCR product was expected to be 221 base pairs. Sequences from which these primers were derived were described by Beyer, et al. [J. Cell Biol. 105:2621–2629 (1987)].

All reaction products were displayed on agarose gels and visualized by ethidium bromide staining as described [Lanson, et al. Cir. 85:1835–1841 (1992)]. In all cases, the PCR products of the appropriate molecular weight were obtained. Controls for the PCR reactions were done to exclude contaminating DNA as the source of the ethidium bands by carrying out the reaction in the absence of reverse transcriptase or by treating the RNA sample with DNase.

Figure 3:
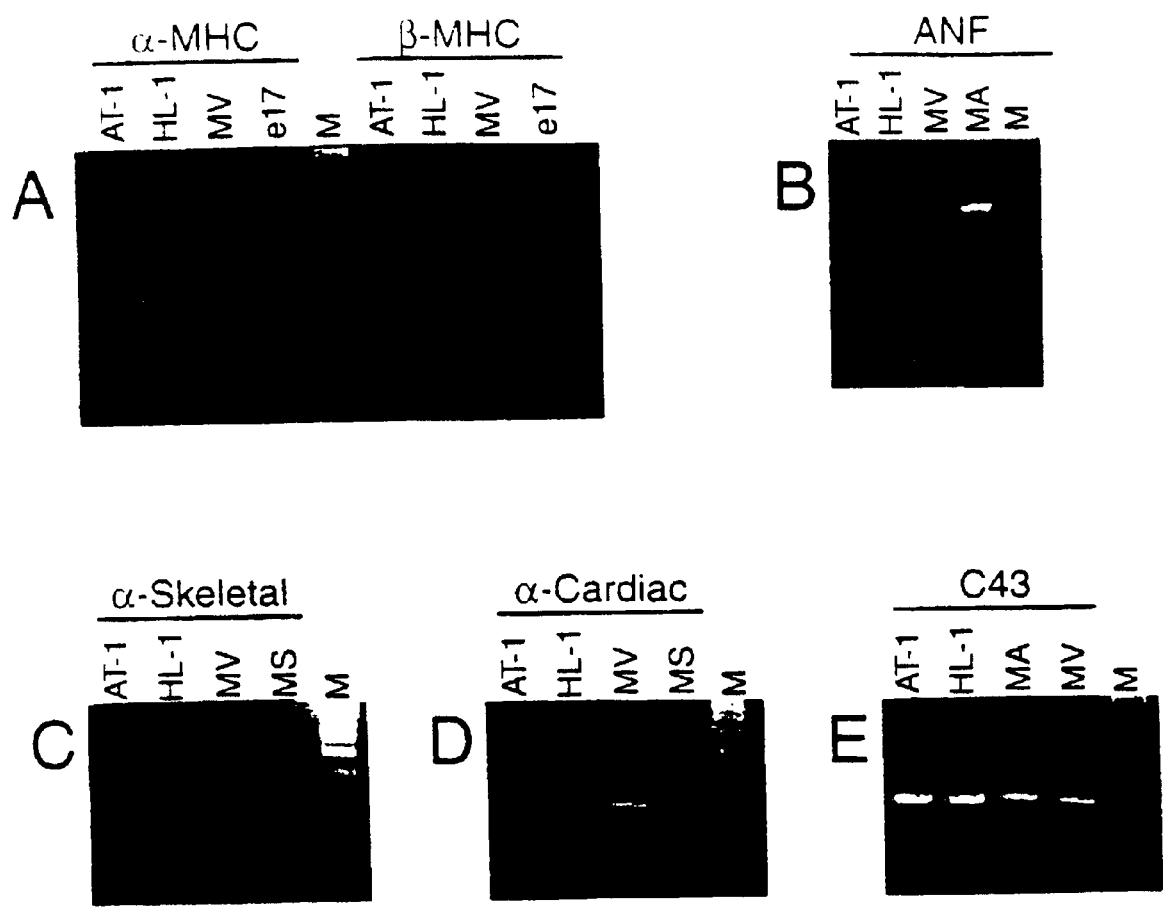
FIGS. 3 a.–e. Identification of cardiac specific genes expressed in HL-cells. Ethidium bromide stain of reverse transcriptase-polymerase chain reaction (RT-PCR) products, separated by agarose gel electrophoresis. Reverse transcriptase-polymerase chain reaction (RT-PCR) products show gene expression of cultured HL-1 cells. Results of RT-PCR based analyses used to examine for the expression of: a. α-myosin heavy chain (α-MHC) and β-myosin heavy chain (β-MHC); b. α-cardiac actin (α-cardiac); c. α-skeletal actin (α-skeletal); d. atrial natriuretic factor (ANF); and e. connexin43 (C43) in controls and cultured HL-1 cells at passage 86. Total RNA was isolated from: AT-1 cells (AT-1), HL-1 cells (HL-1), ventricular cardiac muscle from RAT Day 17 embryonic rat (e17), ventricular cardiac muscle from adult mouse (MV), atrial cardiac muscle from adult mouse (MA), skeletal muscle from adult mouse (MS), (M) DNA molecular weight markers.

The pattern of gene expression of cultured HL-1 cells was similar to that of adult atrial myocytes. As seen in FIG. 3, HL-1 cells expressed atrial natriuretic factor (ANF), α-cardiac myosin heavy chain, α-cardiac actin, and connexin43. These data demonstrate that the HL-1 cells do not express the embryonic β-myosin heavy chain isoform of myosin or skeletal α-actin. These results are consistent with the interpretation that the HL-1 cells have not reverted to an embryonic phenotype.

COMPARISON OF HL-1 CELLS TO AT-1 CELLS

The HL-1 cell line was derived from the AT-1 tumor lineage. AT-1 cells are atrial cardiomyocytes that originated from the left atrium of transgenic mice that express the SV40 large T antigen under control of the ANF promoter in the atria [Delcarpio, et al. Cir. Res. 69:1591–1600 (1991)]. AT-1 cells are isolated from subcutaneous tumors grown in syngeneic mice. AT-1 cells can be easily grown in culture but they cannot be passaged. HL-1 cells are similar to AT-1 cells in the cardiac-specific genes that they express but are not as highly differentiated morphologically as AT-1 cells in culture. HL-1 cells contain fewer atrial granules, and the sarcomeric organization in HL-1 cells is not as well organized as AT-1 cells. A property unique to the HL-1 cell line is that HL-1 cells can be serially passaged in culture. Furthermore, HL-1 cells can be cryopreserved in liquid nitrogen. AT-1 cells cannot be passaged in culture and they can not be cryopreserved. AT-1 cells must be carried as a subcutaneous tumor in syngeneic mice as a tumor lineage. Another unique feature of the HL-1 cell line is that it does not require the use of live animals in order to maintain it in growing form. The HL-1 cells are the only cardiac muscle cell line that can be serially passage in culture and that retains both the morphology and gene expression pattern of adult atrial cardiac muscle cells.

USE OF HL-1 CELLS AS INVESTIGATIONAL TOOLS

Additional studies with HL-1 cells demonstrate their utility as investigational tools. Furthermore, these additional studies have further characterized the HL-1 cells as cardiomyocytes. These data indicate that HL-1 cells possess receptors and intracellular signaling pathways which, in the presence of known pharmacological agents, produce responses consistent with those observed with cardiomyocytes. Consequently, HL-1 cells are a model system in which the effects of novel molecules on cardiomyocytes can be assessed.

EXAMPLE 1

CONTRACTILE ACTIVITY OF HL-1 CELLS

Figure 4:
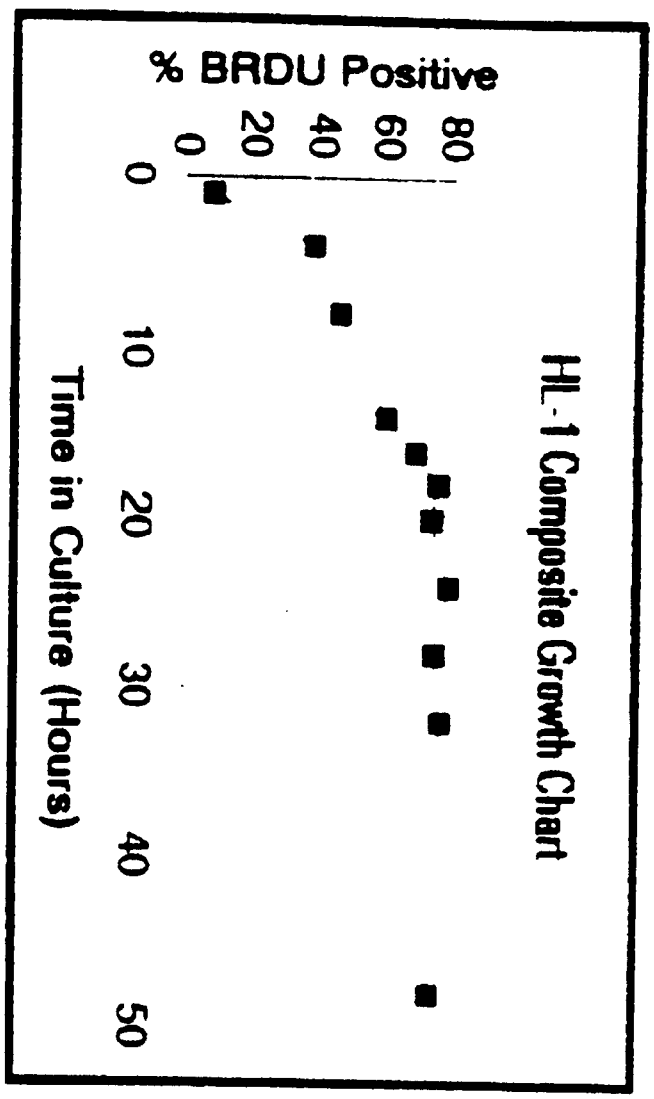
FIG. 4. Action potentials recorded from a spontaneously beating, HL-1 cell: The spontaneous beating rate for this cell was approximately 35 beats per minute. Action potentials were recorded in current clamp mode at room temperature (22–23° C.).

HL-1 cells spontaneously contract in culture. The action potentials recorded from a spontaneously beating HL-1 cell are shown in FIG. 4. The spontaneous beating rate for this cell was approximately 35 beats per minute. Current recordings are performed with an Axopatch 1-D patch-clamp amplifier (Axon Instruments, Foster City, Calif.) in the whole-cell configuration of the current clamp mode. Data acquisition and command potentials are controlled with a commercial software program (PCLAMP, Axon Instruments, Foster City, Calif.). The external solution is normal Tyrode's solution and contained (mmol/L): NaCl 130, KCl 4, $CaCl_2$ 1.8, $MgCl_2$ 1, HEPES10 and glucose10 (pH adjusted to 7.35 with NaOH). The internal (pipette) solution contained (mmol/L): KCl, 110, $K_2ATP$ 5, $K_4BAPTA$ 5, $MgCl_2$ 1, and HEPES10 (pH adjusted to 7.2 with KOH). Microelectrodes are pulled from borosilicate glass (Garner Glass, Claremont, Calif.) and heat-polished (pipette tip resistance, 5–9 MW). Ion currents are recorded at room temperature (22–23° C.).

HL-1 cells are found to respond to several pharmacological agents in a manner expected for cardiomyocytes. Confluent cultures of HL-1 cells at passage 33 in growth medium (without norepinephrine or retinoic acid) display spontaneous contractile activity (beating). After adding norepinephrine bitartrate to a final concentration of $10^{-5}$ M, the cells are observed to be beating faster within two minutes.

In other experiments, spontaneously beating confluent HL-1 cells in growth medium are stopped by adding propranolol. First, norepinephrine bitartrate is added to a final concentration of $10^{-5}$ M. Under these stimulated conditions, propranolol is subsequently added. At a final concentration of $10^{-4}$ M, propranolol arrests all contractions within 10 minutes upon addition of the drug. Propranolol at final concentrations of $10^{-7}$ M, $10^{-6}$ M, and $10^{-5}$ M, has no observable effect on the contractile activity of the HL-1 cells.

To determine if the effect of $10^{-4}$ M propranolol is reversible, the culture medium containing propranolol is removed and growth medium (without norepinephrine or retinoic acid) is added to the cell cultures. Within 1 hour, the HL-1 cells previously exposed to $10^{31\ 4}$ M propranolol display contractile activity similiar to control HL-1 cell not exposed to propranolol. In other experiments, spontaneous beating cultures of spontaneously contracting confluent HL-1 cells in growth medium (without norepinephrine or retinoic acid) are also exposed to verapamil hydrochloride at final concentrations of $10^{-7}$ M, $10^{-6}$ m and $10^{-5}$ M. When viewed after addition of verapamil hydrochloride, all cell cultures receiving drug have no observable contractile activity. These qualitative observations suggest that HL-1 cells display pharmacological responses similar to normal mouse adult cardiomyocytes in culture, including the appropriate responses of functional adrenergic receptors and calcium ion channels.

EXAMPLE 2

BRDU LABELING OF HL-1 CELLS TO MEASURE CELL PROLIFERATION

HL-1 cells at passage 50 are used to investigate BRDU incorporation as a measure of cellular proliferation. In this particular experiment, 100,000 HL-1 cells are plated on gelatin/fibronectin coated coverslips in 12 well plates in 1 ml of ExCell 320 medium which is supplemented with penicillin/streptomycin, 10% FBS, 10 ug/ml Insulin, 2×nonessential amino acids, ECGS, and retinoic acid. At the start of the experiment, the medium is changed to fresh medium and BRDU is added to a final concentration of 10 uM. Two coverslips at each time point are washed 2× with PBS and fixed for 30 min in 95% ethanol/5% acetic acid. They are then washed 3× with PBS for 5 min and stored at 5° C. To detect BRDU incorporation, an Amersham Cell Proliferation kit RPN-20 is used. The labeling reagent is 5-bromo-2'-deoxyuridine and 5-fluoro-2'deoxyuridine (10:1 ratio). The procedure outlined in the kit is followed. The fixed cells are treated with nuclease/anti-5-bromo-2'-deoxyuridine for 1 hr at room temperature and then washed in PBS. Detection of bound antibody is achieved with peroxidase-conjugated antibody to mouse immunoglobulin, incubated at room temperature for 30 min. Diaminobenzidine is then polymerized in the presence of cobalt and nickel giving blue-black staining at sites of BRDU incorporation. About 500 cells/coverslip (total population) are counted to determine the percentage labeled cells.

Figure 5:
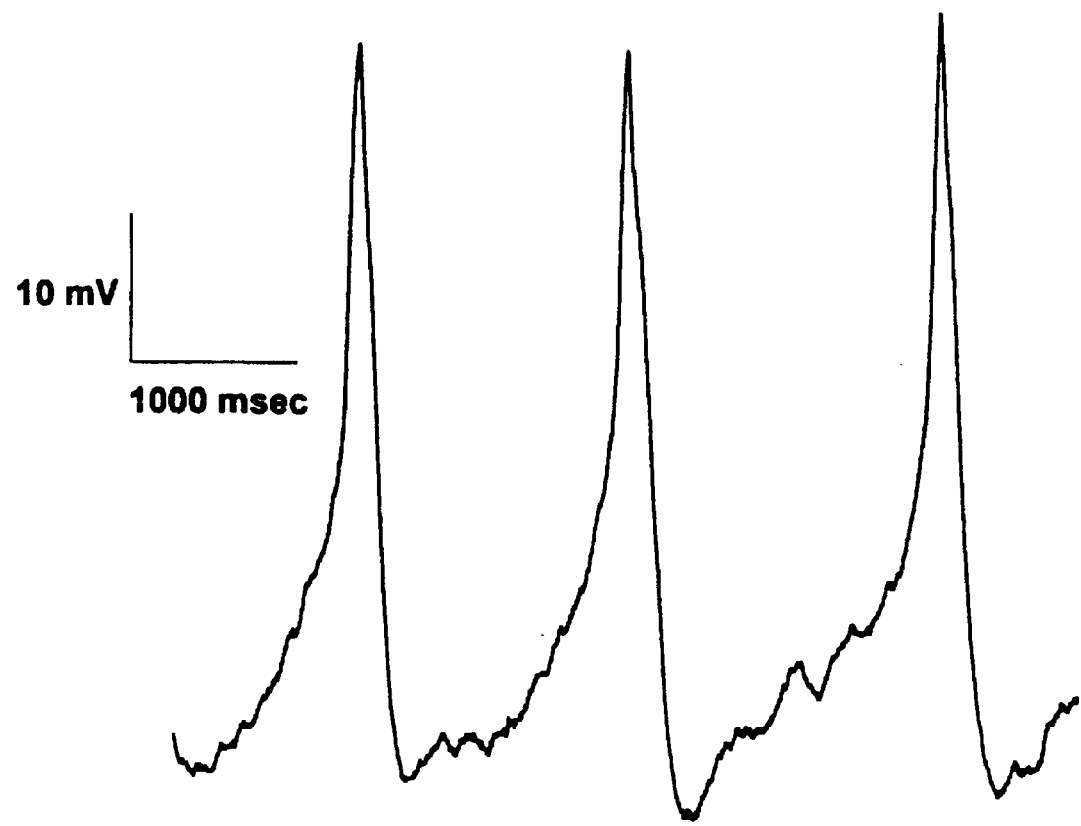
FIG. 5. Incorporation of bromodeoxyuridine (BRDU) by HL-1 cells at passage 50 expressed as the percent of BRDU-positive cells at different times after adding BRDU to the culture medium. By 24 hours approximately 80% of the cells are labeled.

The results of this analysis demonstrate that maximal labeling with BRDU (approximately 80% of the HL-1 cells are positively stained) is achieved by 24 hours. In FIG. 5 is found the BRDU incorporation curve for HL-1 cells at passage 50. The results indicate that the HL-1 cells can be used for assays to measure the proliferation of cardiomyocytes, in vitro.

EXAMPLE 3

UTILITY OF HL-1 CELLS IN ELECTROPHYSIOLOGIC AND PHARMACOLOGIC INVESTIGATIONS

HL-1 cells from passage 60–80 are grown on 5 mm glass coverslips (Bellco Glass, Vineland, N.J.). For electrophysiologic investigation, the glass coverslips are transferred to a chamber mounted on a Nikon Diaphot microscope. Current recordings are performed with an Axopatch 1-D patch-clamp amplifier (Axon Instruments, Foster City, Calif.) in the whole-cell configuration of the patch-clamp technique [Hamill, O. P. et al, *Pflugers Arch. Gen. Physiol.* 391: 85–100 (1981)]. Data acquisition and command potentials are controlled with a commercial software program (PCLAMP, Axon Instruments, Foster City, Calif.). The external solution is normal Tyrode's solution and contained (mmol/L): NaCl 130, KCl 4, $CaCl_2$ 1.8, $MgCl_2$ 1, HEPES10 and glucose10 (pH adjusted to 7.35 with NaOH). The internal (pipette) solution contained (mmol/L): KCl 110, $K_2ATP$ 5, $K_4BAPTA$ 5, $MgCl_2$ 1, HEPES10 (pH adjusted to 7.2 with KOH). Microelectrodes are pulled from borosilicate glass (Garner Glass, Claremont, Calif.) and heat-polished (pipette tip resistance, 5–9 MW). Ion currents are recorded at room temperature (22–23° C.).

Figure 6:
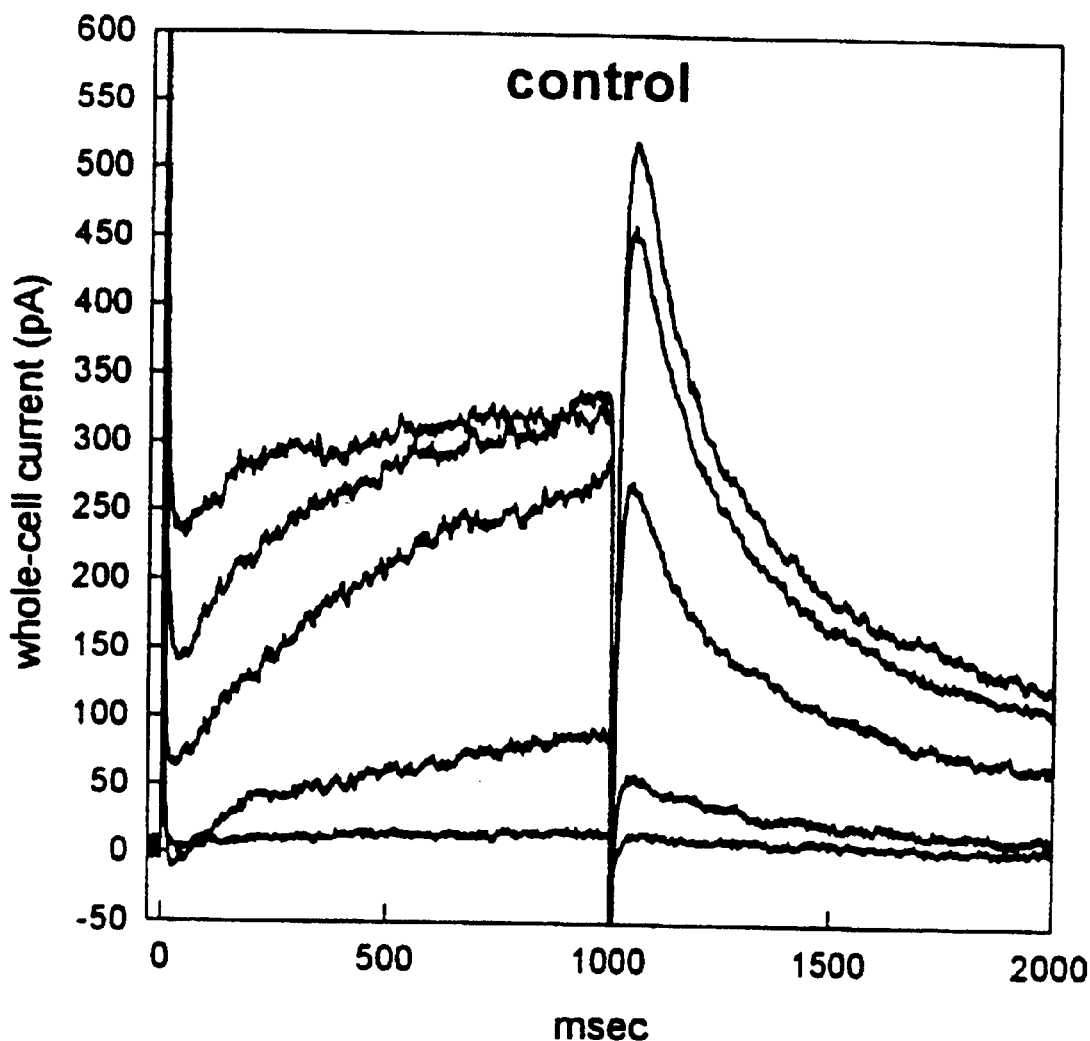
FIGS. 6 and 7. Whole-cell currents from an HL-1 cell in the absence (FIG. 5) and presence (FIG. 6) of 10 $\mu$M dofetilide.

Ion currents are activated by 1 see voltage pulses from a holding potential of −50 mV to potentials between −40 mV to +80 mV in 20 mV increments. The holding potential of −50 mV is used to inactivate $Na^+$ and T-type $Ca^{++}$ currents. 100 μM $Cd^{++}$ is included in the extracellular solution to block L-type $Ca^{++}$ current. The interval between voltage clamp pulses is 10 sec–20 sec. Under these conditions, depolarizing voltage clamp pulses activated a time-dependent outward current. FIG. 6 illustrates whole-cell current recordings from a typical HL-1 cell. Shown are current traces in response to voltage pulses from −40 to +40 mV, in 20 mV increments, from a holding potential of −50 mV. The activating current displays inward rectification, and the deactivating current tails are voltage dependent and saturated at +20 mV to +40 mV. The deactivation kinetics of the tail current are biexponential, similar to $I_{Kr}$ current in cardiac myocytes [Sanguinetti, M. C. and Jurkiewicz, N. K., *J. Gen Physiol.* 96: 195–215 (1990)]. These current characteristics are consistent with those of cardiac $I_{Kr}$. The $I_{Kr}$-like current is the most prominent outward current in HL-1 cells and was found in 61 of 65 cells examined.

Using the same experimental conditions as described above, except that the holding potential was −70 mV and there was no $Cd^{++}$ in the solution, time- and voltage-dependent inward currents are also observed in the HL-1 cells. These are most likely sodium and L-type calcium currents.

Figure 7:
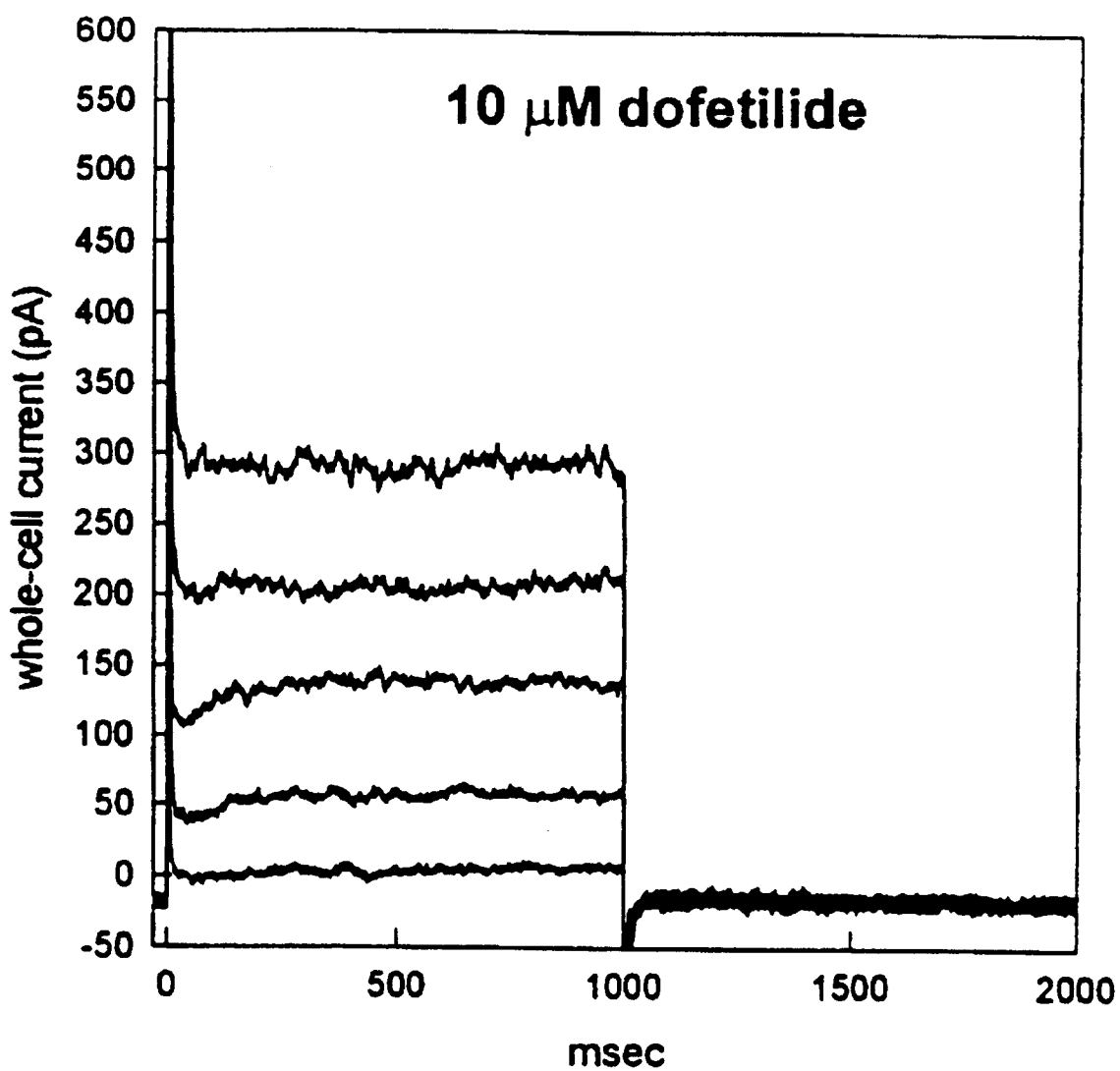
Figure 8:
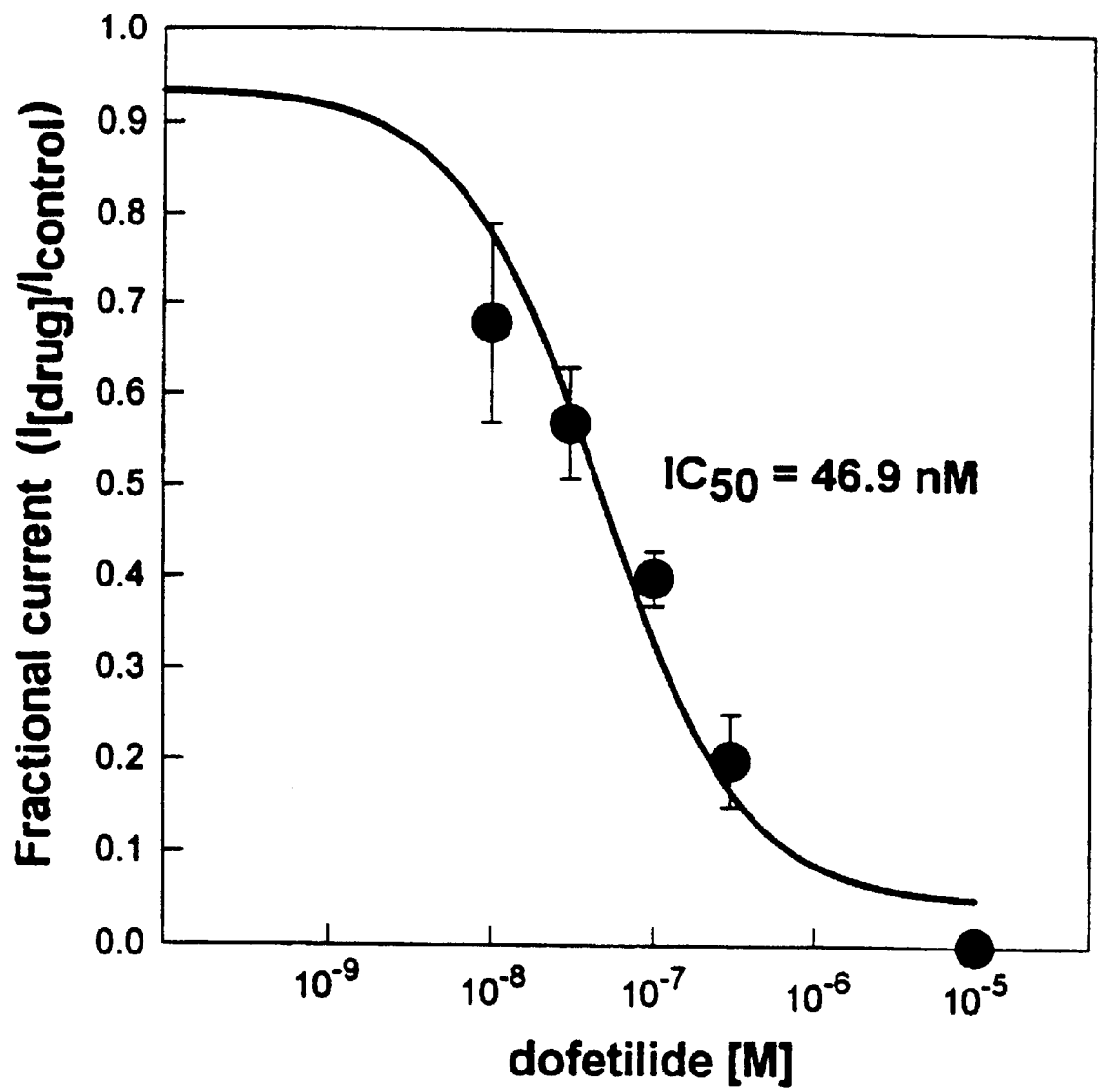
FIG. 8. Concentration-response relationship for block $I_{Kr}$ tail current by dofetilide. $I_{Kr}$ tail currents were elicited during the repolarisation from 1 sec voltage pulses to +20 mV. Plotted are means values±S.E.M. (n32 4). An $IC_{50}$ of 46.9 nM was calculated using a non-linear regression fit. The nanomolar sensitivity of the major outward current in HL-1 cells to dofetilide further identifies it as cardiac $I_{Kr}$.

Methansulfonanilide sensitivity identifies cardiac $I_{Kr}$ due to the high selectively of these compounds for this channel [Jurkiewicz, N. K. and Sanguinetti, M. C., *Circ. Res.* 72:75–83 (1993)]. The methansulfonanilide, dofetilide (10 μM (synthesized according to the method described by Cross, P. E., et al., J. Med. Chem., 33:115 1–5(1990)); n=2) completely abolishes the time-dependent component of the activating current as well as the deactivating tail currents (see FIG. 6). Upon blockade of time-dependent outward current a residual time-dependent outward current is noted in most HL-1 cells (FIG. 7). The ionic nature of the current carrier is not identified. The concentration-response relationship for block of $I_{Kr}$ tail current carrier is not identified. The concentration-response relationship for block of $I_{Kr}$ tail current by dofetilide (P&GP lot number 12623-JE-82F) is determined (FIG. 8). An $IC_{50}$ of 46.9 nM (n=4) was calculated by a non-linear regression fit using GraphPad Prism software (GraphPad, San Diego, Calif.). The $IC_{50}$ observed under our experimental conditions is similar to the $IC_{50}$ reported for $I_{Kr}$ in rabbit ventricular myocytes (4 nM) [Carmeliet, E., *J. Pharmacol. Exp. Ther.* 262: 809–817 (1992)] and guinea pig myocytes (31 nM) [Jurkiewicz, N. K. and Sanguinetti, M. C., *Circ. Res.* 72: 75–83 (1993)]. The nanomolar sensitivity of the major outward current in HL-1 cells to dofetilide further identifies it as cardiac $I_{Kr}$.

These results indicate that HL-1 cells can be used to screen drugs or pharmacological agents that affect the delayed rectifier current: (a) these results confirm electrical character as functional cardiomyocytes in situ; and (b) these results strongly indicate that the HL-1 cell line can be utilized for the discovery of novel cardiac agents and assessment of cardiac agents that interfere with sodium, calcium, potassium currents.

EXAMPLE 4

[³H]DOFETILIDE BINDING

In order to demonstrate that $I_{Kr}$ channels are present in HL-1 cells. [³H]dofetilide binding experiments are performed using a modification of a published method [Chadwick, et al, Circ. Res. 72:707–714, (1992)]. [³H] Dofetilide was synthesized by catalytic hydrogenation of N-[4-[2-[methyl[2-[3-bromo-4-(methylsulfonyl)amino]phenoxy]ethyl]amino]ethyl]phenyl]methanesulfonamide by the following method. To an ice-cold solution of dodetilide hydrochloride [Cross, P. E. et al. J. Med. Chem., 33(4), 1151–5 (1990)] (200 mg, 0.46 mmol) in glacial acetic acid (3 mL) was added $Br_2$ (0.10 mL, 18.4 mmol). After 5 minutes the now heterogeneous mixture was quenched with saturated $NaHSO_3$ (5 mL). The mixture was applied to a rotoevaporator to remove the acetic acid (bath temperature at 60° C). Saturated $NaHCO_3$ (5 mL) was added, followed by methanol (2 mL) to solubilize a gummy purple residue. The mixture was extracted with ethyl acetate (5×15 mL), and the combined organic extracts were dried ($MgSO_4$), filtered, and evaporated to yield the crude bromination product as a purple oil, 194 mg. This material was purified by preparative TLC, eluting twice with $CH_2Cl_2$:methanol (9:1). The band eluting at $R_f$0.55–0.60 was collected to yield a single mono-bromination isomer, 54 mg (22.5%). The structure of this bromination product was assigned on the basis of the small meta coupling constant in the most upfield aromatic resonance (d=6.87), which suggests that monobromination occurred ortho to the methanesulfonanilide moiety of the phenolic ring. Catalytic hydrogenation was performed by New England Nuclear (Boston, Mass.) by reacting the brominated precursor over 10% Pd/C in the presence of ³$H_2$ gas. The final product has a specific activity of 38 Ci/mmol, and has greater than 96% purity as determined by HPLC analysis.

HL-1 cells from passages 60 to 80 are dissociated from tissue culture flasks with a 5 min incubation with 0.1% trypsin (Clonetics, San Diego) followed by inactivation in a trypsin neutralizing solution (Clonetics, San Diego). The cells are suspended in a buffer containing (mM) KCl 40, $KH_2PO_4$ 20, $MgCl_2$ 5, $KHCO_3$ 0.5, glucose 10, potassium glutamate5 0, potassium asparate 20, EGTA 1 and HEPES (N-[2-Hydroxyethyl]piperazine-N'-[2-ethanesulfonic acid]) 10, adjusted to pH 7.4 with KOH and containing 0.1% bovine serum albumin (BSA). Cells (1–2×10⁵ cells per ml) are incubated with [³H]dofetilide in 250 μl of buffer for 30 min at 37° C. The cells are then filtered on GF/C Unifilter® 96 well filter plates (Packard, Meriden, Conn.) using a Packard Micromate496® harvester. Filter plates are pre-soaked with wash buffer (25 mM Tris-HCl, 130 mM NaCl, 5.5 mM KCl, 0.8 mM $MgCl_2$ and 50 μM $CaCl_2$ [pH 7.4]) containing 1.0% BSA and washed following harvesting at room temperature with four ×1 ml washes of the same buffer without BSA. Bound [³H]dofetilide is determined following addition of Microscint-20® (Packard) by liquid scintillation spectroscopy in a Packard TopCount® Scintillation counter. Specific binding, defined as counts bound in the absence of cold dofetilide minus counts bound in the presence of cold dofetilide (20 $\mu$M), is analyzed by non-linear regression fit to either a one site binding hyperbola for saturation binding experiments or by non-linear regression fit to a single site competition curve with GraphPad Prism software (GraphPad, San Diego).

In saturation binding experiments, HL-1 cells (passage 60–70) are incubated at a concentration of $2.4 \times 10^5$ cells per ml with 200, 100, 50, 25, 12.5, or 6.25 nM [$^3$H]dofetilide both with and without 20 $\mu$M unlabeled dofetilide. The binding is saturable, with a $K_d$ of 140+/−60 nM and a $B_{max}$ of 118 fmol per $10^5$ cells. The $K_d$ for [$^3$H]dofetilide binding to HL-1 cells is not significantly different than that determined in guinea pig myocytes (70+/−6 nM, mean+/−SD, n=3; [Chadwick, et al, Circ. Res. 72:707–714, (1992)]).

In competition binding experiments HL-1 cells (2 to $3 \times 10^5$ per ml) from passage 60 to 80 are incubated with 30 to 40 nM [$^3$H]dofetilide and various concentrations of known $I_{Kr}$ blockers: clofilium (Eli Lilly & Co, Indianapolis, lot number T37-KV5-131), azimilide dihydrochloride, (azimilide dihydrochloride is synthesized according to the procedure set forth in U.S. Pat. No. 5,462,940) and dofetilide (synthesized according to the method described by in Cross, P. E., et al., J. Med. Chem. 33:1151–5(1990)). The $K_d$ values determined in HL-1 cells for dofetilide and for clofilium are in agreement with the values obtained in [$^3$H]dofetilide binding experiments on guinea pig myocytes (Table 1). The $K_d$ for azimilide dihydrochloride is in agreement with the $IC_{50}$ for blocking the rapidly activating component of the delayed rectifier $I_{Kr}$ in guinea pig myocytes (0.4 M; [Fermini et al, J. Cardiovasc. Pharmacol. 26: 259–67 (1995)]).

TABLE 1

Competition for [$^3$H] dofetilide binding in HL-1 cells and guinea pig myocytes

| | HL-1 cells | | | Cardiac Myocytes* | |
|---|---|---|---|---|---|
| Drug | N | $K_d(\mu M)$ | SEM($\mu M$) | N | $K_d(\mu M)$ | SEM($\mu M$) |
| dofetilide | 4 | 0.042 | 0.02 | 13 | 0.10 | 0.03 |
| clofilium | 3 | 0.83 | 0.43 | 5 | 1.29 | 0.32 |
| azimilide | 6 | 0.80 | 0.14 | | | |

*Values for dofetilide and clofilium obtained in primary guinea pig myocytes. [Chadwick, et al, Circ. Res. 72:707–714, (1992)].

HL-1 cells possess specific binding sites for [$^3$H] dofetilide, a potent and highly specific ligand for the rapidly activating component of the delayed rectifier channel $I_{Kr}$. The potency of several antiarrhythmic drugs for the [$^3$H] dofetilide binding site in HL-1 cells is similar to that in isolated myocytes. This characteristic allows the use of HL-1 cells for the screening of compounds in competition binding assays to find potential $I_{Kr}$ blocking drugs that may be useful as cardiac active agents, including antiarrhythmic agents.

EXAMPLE 5

GROWTH FACTOR SECRETION BY HL-1 CELLS

In addition to the utility of HL-1 cells for biological screening purposes, these cells may be considered as a source of cellular products. An evaluation of the conditioned media from HL-1 cell cultures has revealed the presence of various growth factors, including basic fibroblast growth factor (bFGF), vascular endothelial growth factor (VEGF), platelet derived growth factor (PDGF), epithelial growth factor (EGF), transforming growth factor (TGF) and adrenomedullin. For these determinations, 15 ml of conditioned medium from HL-1 cells (passage 51) cultured in serum-free medium is concentrated with a Centriprep®-10 (Amicon Corp., Mass.) concentrator column with a 10 Kd molecular weight cutoff. Centrifugation for 1 hour at 3000× g, 4° C. reduces the volume approximately 5 fold and after removing the flowthrough volume, an additional 1 hour centrifugation further reduces the medium volume to 1.5 ml. The concentrated-pooled medium was collected, and 130 microliter aliquots are applied onto a nitrocellulose sheet held in a BioDot®, SF Cell (BioRad, Hercules, Calif.) with a 48 well capacity. The Centriprep®-10 flowthrough is similarly dotted onto the nitrocellulose sheet. Control peptides are also applied onto the nitrocellulose sheet. The amount used per well are listed in Table 2 below.

TABLE 2

| Control | Source |
|---|---|
| Basic FGF-human recombinant basic fibroblast growth factor, carrier free (2.5 ug/dot) | Upstate Biotechnologies Inc., Cat#01–114, lot#13365 |
| VEGF (A-20) control peptide (0.5 ug/dot) | Santa Cruz Biotechnology, Cat#SC-152P, lot#J214 |
| EGF-mouse epidermal growth factor (0.5 ug/dot) | Upstate Biotechnologies Inc., Cat#01–102, lot#13061 |
| PDGF-human platelet derived growth factor, A:B heterodimer (0.75 ug/dot) | Upstate Biotechnologies Inc., Cat#01–310, lot#14430 |
| TGF-transforming growth factor 1(V) (0.5 ug/dot) | Santa Cruz Biotechnology, Cat#SC-146P, lot#A174 |
| adrenomedullin (0.1 ug/dot) | Phoenix Pharmaceuticals, Cat#010–08, lot#410521 |

After allowing the samples to dry, the nitrocellulose sheet is removed from the BioDot®, SF Cell and blocked with 30% bovine serum albumin (BSA) in 20 mM TriCl, pH 7.4, 200 mM NaCl (TBS) overnight at 4° C. The membrane is rinsed 3×10 min. in 0.1% Tween in TBS. The nitrocellulose sheet is then cut to separate the fractions for treatment with the different primary antibody solutions. Incubation with primary antibody is for 2 hours at room temperature. The primary and secondary antibodies used are listed in Table 3 below.

TABLE 3

| 1° antibody | 1° antibody source | 2° antibody | 2° antibody source |
| --- | --- | --- | --- |
| Anti-bovine basic FGF, type II, monoclonal mouse IgG$_{1K}$ (1:2000) | Upstate Biotechnologies Inc., Cat#05–118, lot#13707 | Anti-mouse IgG (Fab specific), peroxidase conjugate (1:4000) | SIGMA Immunochemicals, lot#083H4808 |
| Anti-human VEGF (A-20) rabbit polyclonal IgG (1:150) | Santa Cruz Biotechnology, Cat#SC-152, lot#D265 | Anti-rabbit IgG (whole molecule), peroxidase conjugate (1:4000) | SIGMA Immunochemicals, lot#082H4810 |
| Anti-mouse EGF, rabbit polyclonal IgG (1:62) | Upstate Biotechnologies Inc., Cat#06–102, lot#10753 | Anti-rabbit IgG (whole molecule), peroxidase conjugate (1:4000) | SIGMA Immunochemicals, lot#082H4810 |
| Anti-human PDGF-A:B, goat polyclonal IgG (1:500) | Upstate Biotechnologies Inc., Cat#06–127, lot#13822 | Anti-goat IgG (whole molecule), peroxidase conjugate (1:4000) | SIGMA, Immunochemicals, lot#093H4819 |
| Anti-TGF(V), rabbit polyclonal IgG (1:150) | Santa Cruz Biotechnology, Cat#SC-146, lot#K154 | Anti-rabbit IgG (whole molecule), peroxidase conjugate (1:4000) | SIGMA Immunochemicals, lot#082H4810 |
| Anti-rat adrenomedullin (1–50), rabbit serum (1:750) | Phoenix Pharmaceuticals, Cat#H-010-08, lot#410384 | Anti-rabbit IgG (whole molecule), peroxidase conjugate (1:4000) | SIGMA Immunochemicals, lot#082H4810 |

Primary and secondary antibodies are diluted in 3% BSA in TBS. Primary antibody is washed off by rinsing the nitrocellulose 3×10 in 0.1% Tween in TBS. Each blot is treated with the appropriate secondary antibody for 2 hours at room temperature. Following a rinse step as before, the dots are developed with a solution of 3,3'-diaminobenzidine tetrahydrochloride (Sigma Fast™ DAB tablets, lot 0844-8943). The reactions are stopped by rinsing the wells with distilled and deionized water. The various control peptides all give a positive reaction to the corresponding antibody. With the exception of adrenomedullin, the Centriprep®-10 flowthrough gives a negative response to all antibodies. With the adrenomedullin antibody, the flowthrough produces a faint signal upon treatment with the peroxidase substrate. In all cases the conditioned media produces positive responses against the different primary antibodies for the growth factors and adrenomedullin. These data demonstrate that the HL-1 cells secrete known growth factors including basic fibroblast growth factor, vascular endothelial growth factor, platelet derived growth factor, epithelial growth factor, transforming growth beta-1 and adrenomedullin. The HL-1 cells may also represent a source of other potentially novel growth factors and other biologically active molecules.

What is claimed is:

1. A cell-line, HL-1, deposited with the American Type Culture Collection under Accession Number CRL-12197.

2. A method for screening the effect of drugs or pharmacological agents comprising the step of exposing a culture of the cell line of claim 1 with the drug or pharmacological agent to be evaluated followed by an assessment of the effect.

3. A method for testing the effect of cardiac actives comprising the step of exposing a culture of the cell line of claim 1 to a cardiac active followed by an assessment of the effect.

4. A method for producing growth factors comprising the steps of
   (a) culturing the cells of claim 1 to provide conditioned medium; and
   (b) collecting the conditioned medium.

5. A method for screening pharmacological agents for their effect on the delayed rectifier current comprising the steps of:
   (a) culturing the cells of claim 1;
   (b) exposing the culture to the pharmacological agent to be screened; and
   (c) measuring the effect on the delayed rectifier current in the cells.

* * * * *